US010088455B2

(12) United States Patent
Maalouf et al.

(10) Patent No.: US 10,088,455 B2
(45) Date of Patent: Oct. 2, 2018

(54) TERMINAL CRIMPING DEVICES

(71) Applicant: Tyco Electronics Corporation, Berwyn, PA (US)

(72) Inventors: Khalil John Maalouf, Chambersburg, PA (US); John Dunaway Charlton, Harrisburg, PA (US); David Michael Stull, Etters, PA (US); Charles David Fry, New Bloomfield, PA (US)

(73) Assignee: TE CONNECTIVITY CORPORATION, Berwyn, PA (US)

( * ) Notice: Subject to any disclaimer, the term of this patent is extended or adjusted under 35 U.S.C. 154(b) by 449 days.

(21) Appl. No.: 14/296,328

(22) Filed: Jun. 4, 2014

(65) Prior Publication Data
US 2015/0357781 A1    Dec. 10, 2015

(51) Int. Cl.
*B23P 19/00* (2006.01)
*H01R 43/042* (2006.01)
(Continued)

(52) U.S. Cl.
CPC .......... *G01N 29/11* (2013.01); *G01N 29/343* (2013.01); *G01N 29/4427* (2013.01);
(Continued)

(58) Field of Classification Search
CPC .. G01N 29/11; G01N 29/343; G01N 29/4427; G01N 2291/2698;
(Continued)

(56) References Cited

U.S. PATENT DOCUMENTS 4,856,186 A    8/1989  Yeomans
5,123,165 A    6/1992  Strong et al.
(Continued)

FOREIGN PATENT DOCUMENTS

WO    WO2012/106390    8/2012

OTHER PUBLICATIONS

Kramer, K. E., et al, "A Method for the Verification of Wire Crimp Compression Using Ultrasonic Inspection", Research in Nondestructive Evaluation, Jan. 29, 2010, pp. 18-29, vol. 21, No. 1, Hampton, VA, USA.
(Continued)

*Primary Examiner* — Donghai D Nguyen

(57) ABSTRACT

A terminal crimping device includes crimp tooling comprising an anvil and a ram. A crimp zone is defined between the anvil and the ram. The crimp zone is configured to receive a wire and a terminal. The crimp tooling crimps the terminal to the wire during a crimp stroke. The terminal crimping device also includes an ultrasonic transducer module having at least one ultrasonic transducer held by at least one of the anvil or the ram. The ultrasonic transducer generates a plurality of ultrasonic pulses during the crimp stroke and directs the ultrasonic pluses through the terminal. The ultrasonic transducer receives the ultrasonic pulses and generates ultrasonic data based on the received ultrasonic pulses. The terminal crimp tooling also includes a crimp quality module communicatively coupled to the ultrasonic transducer module. The crimp quality module performs coherent processing of the ultrasonic data to determine a crimp quality.

20 Claims, 4 Drawing Sheets

(51) Int. Cl.
 *G01N 29/11* (2006.01)
 *G01N 29/34* (2006.01)
 *G01N 29/44* (2006.01)
 *H01R 43/048* (2006.01)

(52) U.S. Cl.
 CPC ....... *H01R 43/048* (2013.01); *H01R 43/0486* (2013.01); *G01N 2291/2698* (2013.01); *Y10T 29/53022* (2015.01)

(58) Field of Classification Search
 CPC .............. H01R 43/0486; H01R 43/048; Y10T 29/53022; Y10T 29/53039; Y10T 29/53087; Y10T 29/5313; Y10T 29/53209; Y10T 29/53235; B30B 15/0094
 USPC ..... 29/720, 747.748, 751, 753; 72/9.5, 17.2, 72/19.8
 See application file for complete search history.

(56) References Cited

U.S. PATENT DOCUMENTS

| | | | |
|---|---|---|---|
| 5,197,186 A | 3/1993 | Strong et al. | |
| 5,271,254 A * | 12/1993 | Gloe | B30B 15/0094 29/705 |
| 7,181,942 B2 | 2/2007 | Yost et al. | |
| 8,490,463 B2 | 7/2013 | Yost et al. | |
| 8,671,551 B2 * | 3/2014 | Yost | H01R 43/0486 29/407.05 |
| 2012/0060585 A1 | 3/2012 | Yost et al. | |
| 2012/0192407 A1 | 8/2012 | Yost et al. | |
| 2013/0197823 A1 | 8/2013 | Williams | |

OTHER PUBLICATIONS

International Search Report, International Application No. PCT/US2015/033725, International Filing Date, Jun. 2, 2015.

\* cited by examiner

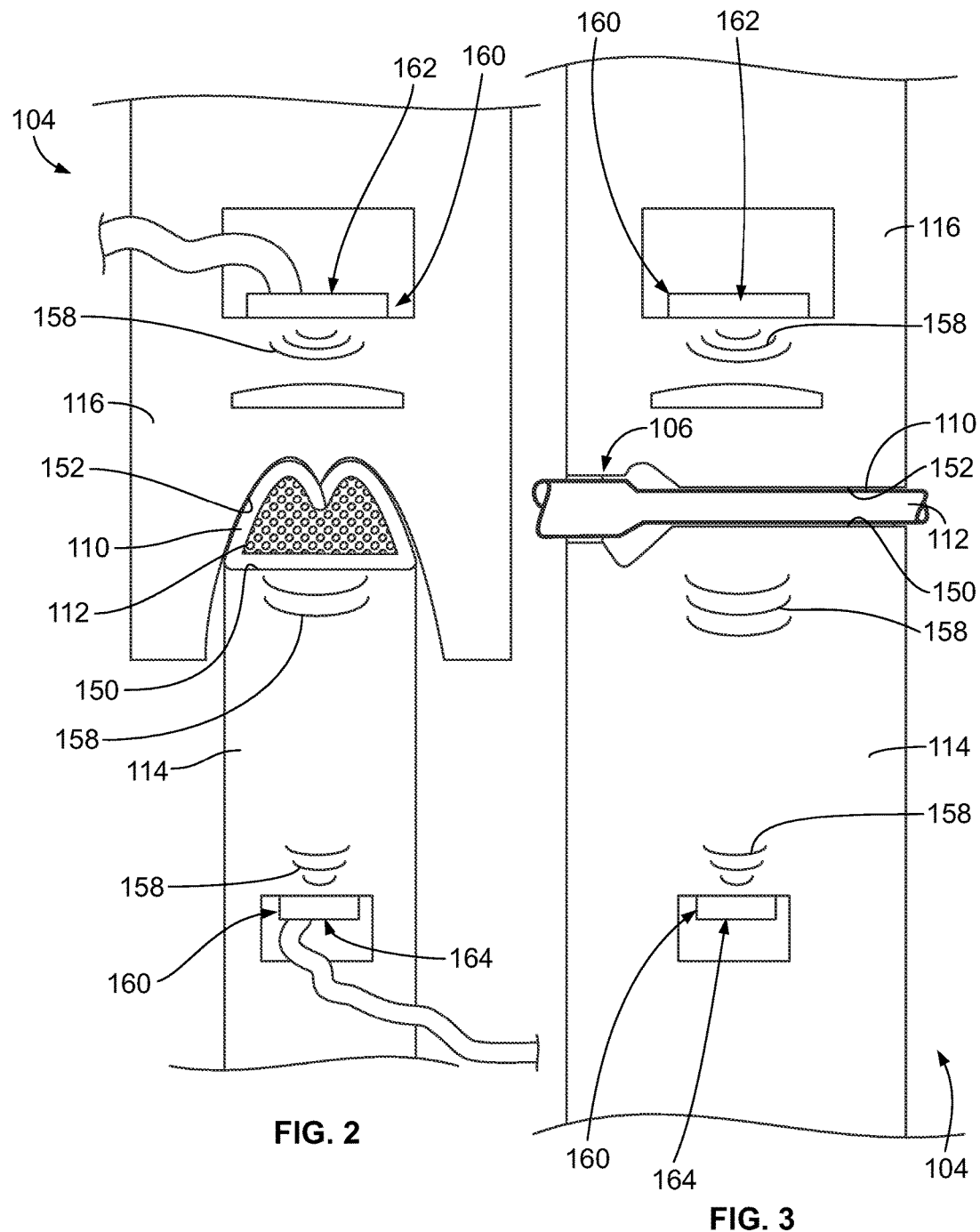

TERMINAL CRIMPING DEVICES

BACKGROUND OF THE INVENTION

The subject matter herein relates generally to terminal crimping devices using ultrasonic transducers.

Terminals are typically crimped onto wires by means of a conventional crimping press having an anvil for supporting the electrical terminal and a ram that is movable toward and away from the anvil for crimping the terminal. In operation, a terminal is placed on the anvil, an end of a wire is inserted into the ferrule or barrel of the terminal, and the ram is caused to move toward the anvil to the limit of the stroke of the press, thereby crimping the terminal onto the wire. The ram is then retracted to its starting point.

New technologies in ultrasonic monitoring have been proposed for use in crimp quality monitoring. For example, U.S. Pat. Nos. 7,181,942 and 8,490,463 describe ultrasonic devices and methods for measuring crimp connections by comparing signals with signals from a previous crimp that was determined to be desirable through destructive testing.

Such ultrasonic monitoring systems are not without disadvantages. For instance, the ultrasonic monitoring systems typically measure the quality of the crimp by transmitting the ultrasonic signals when the ram is at a bottom limit of the stroke of the press. While the ultrasonic signals sampled at the bottom limit of the stroke provide one indicator of the quality of the crimp, the measurement does not reveal defects inside of the crimp that may have been created before the crimp is fully developed. The defects may be caused by factors such as using the wrong terminal or wire size, missing strands of wire, using the wrong wire type, incorrect stripping of insulation, and/or the like. Since such defective crimped connections frequently have the appearance of high quality crimp connections, it is difficult to identify these defects so that timely corrective action may be taken.

A need remains for a crimp quality monitoring system that uses ultrasonic monitoring to determine crimp quality.

BRIEF DESCRIPTION OF THE INVENTION

In an embodiment, a terminal crimping device is provided. The terminal crimping device includes crimp tooling comprising an anvil and a ram. A crimp zone is defined between the anvil and the ram. The crimp zone is configured to receive a wire and a terminal. The crimp tooling crimps the terminal to the wire during a crimp stroke. The terminal crimping device also includes an ultrasonic transducer module having at least one ultrasonic transducer held by at least one of the anvil or the ram. The ultrasonic transducer generates a plurality of ultrasonic pulses during the crimp stroke and directs the ultrasonic pluses through the terminal. The ultrasonic transducer receives the ultrasonic pulses and generates ultrasonic data based on the received ultrasonic pulses. The terminal crimp tooling also includes a crimp quality module communicatively coupled to the ultrasonic transducer module. The crimp quality module performs coherent processing of the ultrasonic data to determine a crimp quality.

In another embodiment, a terminal crimping device is provided. The terminal crimping device includes crimp tooling comprising an anvil and a ram. A crimp zone is defined between the anvil and the ram. The crimp zone is configured to receive a wire and a terminal. The crimp tooling crimps the terminal to the wire during a crimp stroke. The crimp stroke has a crimping phase that begins after initial contact between the ram and the terminal to when the ram is fully engaged with the anvil at a bottom dead center of the crimp tooling, a retracting phase that begins after the crimp tooling reaches bottom dead center, and a release phase that begins after the ram releases the terminal. The terminal crimping device also includes an ultrasonic transducer module having at least one ultrasonic transducer held by at least one of the anvil or the ram. The ultrasonic transducer generates a plurality of ultrasonic pulses during the crimp stroke and directs the ultrasonic pulses through the terminal. The ultrasonic transducer receives the ultrasonic pulses and generates ultrasonic data based on the received ultrasonic pulses. The terminal crimping device includes a crimp quality module communicatively coupled to the ultrasonic transducer module. The crimp quality module performs coherent processing of the ultrasonic data to determine a crimp quality.

In another embodiment, a terminal crimping device is provided. The terminal crimping device includes crimp tooling comprising an anvil and a ram. A crimp zone is defined between the anvil and the ram. The crimp zone is configured to receive a wire and a terminal. The crimp tooling crimping the terminal to the wire during a crimp stroke. The terminal crimping device also includes an ultrasonic transducer module having at least one ultrasonic transducer held by at least one of the anvil or the ram. The ultrasonic transducer module generates a plurality of ultrasonic pulses over a plurality of frequency bands during the crimp stroke and directs the ultrasonic pulses through the terminal. The plurality of frequency bands include a high frequency band and a low frequency band. The ultrasonic transducer module receives the ultrasonic pulses and generates ultrasonic data based on the received ultrasonic pulses. The terminal crimping device also includes a crimp quality module communicatively coupled to the ultrasonic transducer module. The crimp quality module performs coherent processing of the ultrasonic data in at least one of the frequency bands to determine a crimp quality. The crimp quality module performs filtering of the ultrasonic data in at least one of the high frequency band or the low frequency band.

BRIEF DESCRIPTION OF THE DRAWINGS

FIG. 2 illustrates a portion of crimp tooling showing an anvil and a ram used to form a crimp during a crimping operation in accordance with an embodiment.

FIG. 3 is a side view of crimp tooling with a terminal and a wire positioned in a crimp zone in the terminal crimping device shown in FIG. 2 in accordance with an embodiment.

DETAILED DESCRIPTION OF THE INVENTION

Figure 1:
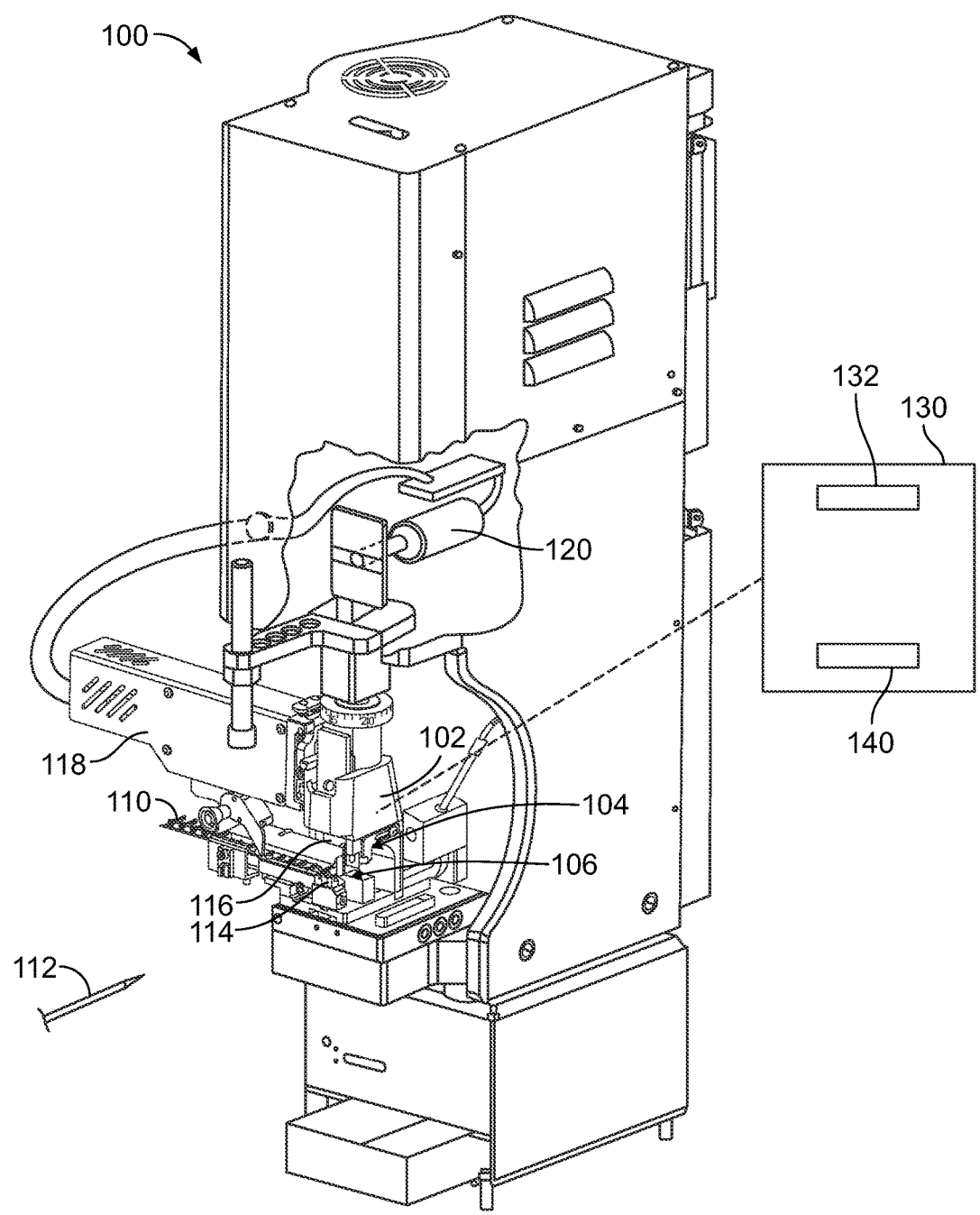
FIG. 1 is a perspective view of a terminal crimping device formed in according to an exemplary embodiment.

FIG. 1 is a perspective view of a terminal crimping device 100 formed in accordance with an exemplary embodiment. The terminal crimping device 100 is used for crimping terminals to wires. In the illustrated embodiment, the terminal crimping device 100 is a bench machine having an applicator 102. Alternatively, the terminal crimping device 100 may be another type of crimping machine, such as a lead maker or a hand tool.

The terminal crimping device 100 includes crimp tooling 104 that is used to form the terminal during the pressing or crimping operation. In an exemplary embodiment, the crimp tooling 104 used for crimping includes an anvil 114 and a ram 116. The terminal crimping device 100 has a terminating zone or crimp zone 106 defined between the anvil 114 and the ram 116. Electrical connectors or terminals 110 and an end of a wire 112 are presented in the crimp zone 106 between the crimp tooling 104. The crimp tooling 104 crimps the terminal 110 to the wire 112 during a crimp stroke. The anvil 114 and/or the ram 116 may have removable dies that define the shape or profile of the terminal 110 during the crimping process. In the illustrated embodiment, the anvil 114 is a stationary component of the applicator 102, and the ram 116 represents a movable component. Alternatively, both the ram 116 and the anvil 114 may be movable. For example, with hand tools, typically both halves of the crimp tooling 104 are closed toward each other during the crimping operation.

The terminal crimping device 100 includes a feeder device 118 that is positioned to feed the terminals 110 to the crimp zone 106. The feeder device 118 may be positioned adjacent to the mechanical crimp tooling 104 in order to deliver the terminals 110 to the crimp zone 106. The terminals 110 may be guided to the crimp zone 106 by a feed mechanism to ensure proper placement and orientation of the terminal 110 in the crimp zone 106. The wire 112 is delivered to the crimp zone 106 by a wire feeder (not shown).

The terminal crimping device 100 may be configured to operate using side-feed type applicators and/or end-feed type applicators. Side-feed type applicators crimp terminals that are arranged side-by-side along a carrier strip, while end-feed type applicators crimp terminals that are arranged successively, end-to-end on a carrier strip. The terminal crimping device 100 may be configured to accommodate both side-feed and end-feed types of applicators, which may be interchangeable within the terminal crimping device 100.

The crimp tooling 104 crimps the terminal 110 to the wire 112 during a crimp stroke. The crimp stroke has both a downward component and an upward component. During the crimp stroke, the ram 116 of the applicator 102 is driven through a crimp stroke by a driving mechanism 120 of the terminal crimping device 100 initially towards the stationary anvil 114 and then away from the anvil 114. The crimping of the terminal 110 to the wire 112 occurs during the downward component of the crimp stroke and includes several phases. The crimp stroke begins with the ram 116 positioned at an upper or initial starting point. Then, a terminal 110 is loaded onto the anvil 114 in the crimp zone 106, and an end of the wire 112 is fed within a crimp barrel of the terminal 110. After the terminal is loaded, a meeting phase begins as the ram 116 is driven downward along the crimp stroke towards the anvil 114 and ends when the ram 116 makes contact with the terminal 110. The crimp phase begins after the ram 116 makes contact with the terminal 110. During the crimp phase, the crimp tooling 104 crimps the terminal 110 onto the wire 112 by compressing or pinching the terminal 110 between the ram 116 and the anvil 114. The ram 116 engages and deforms (e.g. folds or rolls) the ends of the crimp barrel inward around the wire 112. Once the ram 116 reaches an apogee at the bottom dead center, a retracting phase begins. After reaching the bottom dead center, the ram 116 changes direction and returns to an upward position. In other words, the retracting phase begins after the ram 116 begins to move away from the anvil 114. As the ram 116 moves upward, the ram 116 eventually releases or separates from the terminal 110 indicating the start of the release phase. In an exemplary embodiment, the resilient nature of the terminal 110 and/or wires 112 causes the terminal 110 to rebound slightly from the bottom dead center of the downward portion of the crimp stroke. The elastic yield or spring back of the terminal 110 will follow the ram 116 for a portion of the return or upward part of the stroke of the ram 116 until the terminal 110 reaches a final or stable size. The ram 116 may then return to the initial starting point after which the crimp stroke may be repeated to crimp another terminal to another wire.

A control module 130 controls the operation of the terminal crimping device 100. For example, the control module 130 may control the operation of the driving mechanism 120. The control module 130 may control the operation of the feeder device 118 and synchronizes the timing of the crimp stroke with the timing of a feed stroke of the feeder device 118.

The control module 130 includes and/or communicates with an ultrasonic transducer module 140 for transmitting and/or receiving ultrasonic signals. The ultrasonic transducer module 140 generates a plurality of ultrasonic pulses 158 (shown in FIGS. 2 and 3) to be transmitted through the terminal 110 and the wire 112 during the crimp stroke to generate ultrasonic data based on ultrasonic pulses received by the ultrasonic transducer module 140. The ultrasonic transducer module 140 may digitize and/or analyze the received ultrasonic pulses. The ultrasonic transducer module 140 and/or the control module 130 may determine a quality of the crimp based on the received ultrasonic pulses 158. In various embodiments, the control module 130 includes a plurality of transducer modules 140.

In an exemplary embodiment, the control module 130 and/or the ultrasonic transducer module 140 includes a crimp quality module 132 that determines a crimp quality of the particular crimp as discussed below. The crimp quality module 132 may be communicatively coupled to the ultrasonic transducer module 140 such that the crimp quality module 132 receives ultrasonic data generated from the transducer module 140 during the crimp stroke. The crimp quality module 132 determines the crimp quality based on the ultrasonic data generated by the ultrasonic transducer module 140. The crimp quality module 132 may perform coherent processing of the ultrasonic data to determine the crimp quality. Coherent processing involves processing of multiple points of ultrasound data for a given crimp. Coherent processing may represent inter-pulse analysis over many different pulses such that coherency between pulses is maintained. Coherency may be maintained by keeping a relationship between pulses such that the pulses are not independent of one another. Coherent processing may be used to determine one or more discriminators including at least one of determination of maximum energy, an integral of energy over time, or a statistical performance metric. For example, the statistical performance metric may include an average, standard deviation, mean, and/or the like. The terminal 110 may be discarded if the crimp quality does not meet certain specifications.

FIG. 2 illustrates a portion of the crimp tooling 104 showing the anvil 114 and the ram 116 used to form the crimp during the crimping operation. FIG. 3 is a side view of the crimp tooling 104 with the terminal 110 and wire 112 positioned in the crimp zone 106. The crimp tooling 104 forms an F-crimp in the illustrated embodiment; however other crimp tooling may form crimps having other shapes in alternative embodiments.

The anvil 114 has a support surface 150 used to support the terminal 110. In the illustrated embodiment, the support surface 150 is flat and horizontal; however the support surface 150 may have other shapes and orientations in alternative embodiments. The terminal 110 rests on the support surface 150 as the ram 116 is moved through the crimp stroke.

The ram 116 has a forming surface 152 that engages the terminal 110 during the crimping process. As ram 116 moves toward the anvil 114, the forming surface 152 presses the sidewalls of the terminal barrel inward forming the crimp. In other words, the forming surface 152 compresses the sidewalls against the wire 112 during the crimping process.

In an exemplary embodiment, the ultrasonic transducer module 140 (shown in FIG. 1) includes at least one ultrasonic transducer generally shown at 160 that transmits and/or receives ultrasonic pulses 158 in the ultrasonic frequency range. In the illustrated embodiment, the ultrasonic transducer module 140 includes an ultrasonic transmitting transducer 162 and an ultrasonic receiving transducer 164. The ram 116 may hold the ultrasonic transmitting transducer 162, while the anvil 114 may hold the ultrasonic receiving transducer 164 or vice versa. For example, in some embodiments, the transmitting transducer 162 in the ram 116 may generate the ultrasonic pulses 158 which are then transmitted through the ram 116, through the terminal 110, and the wire 112, then through the anvil 114, where the ultrasonic pulses 158 are received by the receiving transducer 164. In other embodiments, the ultrasonic receiving transducer 164 may be coupled to the ram 116 and/or the ultrasonic transmitting transducer 162 may be coupled to the anvil 114. In other embodiments, rather than having dedicated transmitting and receiving transducers, either or both of the transducers 162, 164 may be capable of transmitting and receiving the ultrasonic pulses 158. In other embodiments, only one transducer 160 is provided and is configured as a transmitter/receiver or transceiver, which may operate in an echo mode capable of transmitting and receiving the ultrasonic pulses 158.

The ultrasonic transducers 160 may be coupled to an outer surface of the crimp tooling 104. Alternatively, the ultrasonic transducers 160 may be embedded within the crimp tooling 104. The ultrasonic transducers 160 are ultrasonically coupled to the crimp tooling 104, wherein the ultrasonic pulses 158 may be transmitted to or from the ultrasonic transducers 160 to or from the crimp tooling 104. The ultrasonic transducers 160 are ultrasonically coupled to the terminal 110 and wire 112 via the crimp tooling 104.

In an exemplary embodiment, the ultrasonic transducers 160 are piezoelectric transducers that, when transmitting, convert electrical energy into sound energy and when receiving, convert sound energy into electrical energy. The piezoelectric transducers change size when a voltage is applied thereto. The ultrasonic transducer module 140 includes electric circuitry coupled to the transmitting transducer 162 to supply a stimulus voltage across the transmitting transducer 162 to cause oscillation at various frequencies to produce sound waves. For example, a stimulus voltage may be supplied to the transmitting transducer 162 to cause the transmitting transducer 162 to resonate at various frequencies. The receiving transducer 164 generates a voltage when force is applied thereto from the ultrasonic pulses 158, and the electric signal generated at the receiving transducer 164 is transmitted by electric circuitry coupled thereto to the ultrasonic transducer module 140 and/or the crimp quality module 132 (shown in FIG. 1). The ultrasonic transducer module 140 then produces ultrasonic data representing a measure of the energy associated with the ultrasonic pulses 158. Other types of ultrasonic transducers 160 other than piezoelectric transducers may be used in alternative embodiments, such as magnetostrictive transducers.

In an exemplary embodiment, the ultrasonic transducer module 140 is used to perform coherent processing of ultrasonic data generated by the ultrasonic pulse 158 at the receiving transducer 164. Coherent processing refers to signal data processing of multiple pulses or data points, such as ultrasonic data before, during, and after the crimp is formed. Coherent processing may be performed during substantially the entire crimping process of the crimp stroke from initial contact of the ram 116 with the terminal 110 until release of the ram 116 from the terminal 110. For example, in one embodiment, the crimp quality module 132 performs coherent processing during a time period prior to the retracting phase to a time period after the retracting phase and encompasses multiple pulses during these time periods. The transmitting transducer 162 delivers a plurality of ultrasonic pulses 158 throughout the crimp stroke. For example, the transmitting transducer 162 may deliver the ultrasonic pulses 158 at a rate of at least 3 or more pulses during the crimping process. As another example, the transmitting transducer 162 may deliver 1000 pulses per second or more. The ultrasonic pulses 158 travel through the crimp tooling 104 and the terminal 110 and the wire 112 in the form of longitudinal sound waves, however the waves may be propagated in any direction. The ultrasonic receiving transducer 164 receives the ultrasonic pulses 158 and converts such signals to electrical signals for coherent processing by the crimp quality module 132.

Defects in the crimp affect the ultrasonic data. The defects may be caused by various factors such as using the wrong terminal or wire size, missing strands of wire, wrong wire type, and incorrect stripping of insulation and/or the like. For example, the wire 112 may comprise a bundle of conductive strands. One or more of the strands may not be fully encapsulated with the terminal 110, thus creating a void. The void may cause the ultrasonic pulse 158 to reflect or refract away from the receiving transducer 164, or otherwise lead to a loss of energy propagation to and through the wire 112 and/or the terminal 110. Such void may be more evident at different times, such as during the crimp phase, and more particularly, at the beginning of the crimp phase. The void may be filled in during the crimping process and, as such, may not be detected at the retracting phase. Thus, the defect may not be evidenced in the fully crimped terminal 110. By using coherent processing, the defect may be detected earlier in the crimping process, for example, during the crimping phase.

Figure 4:
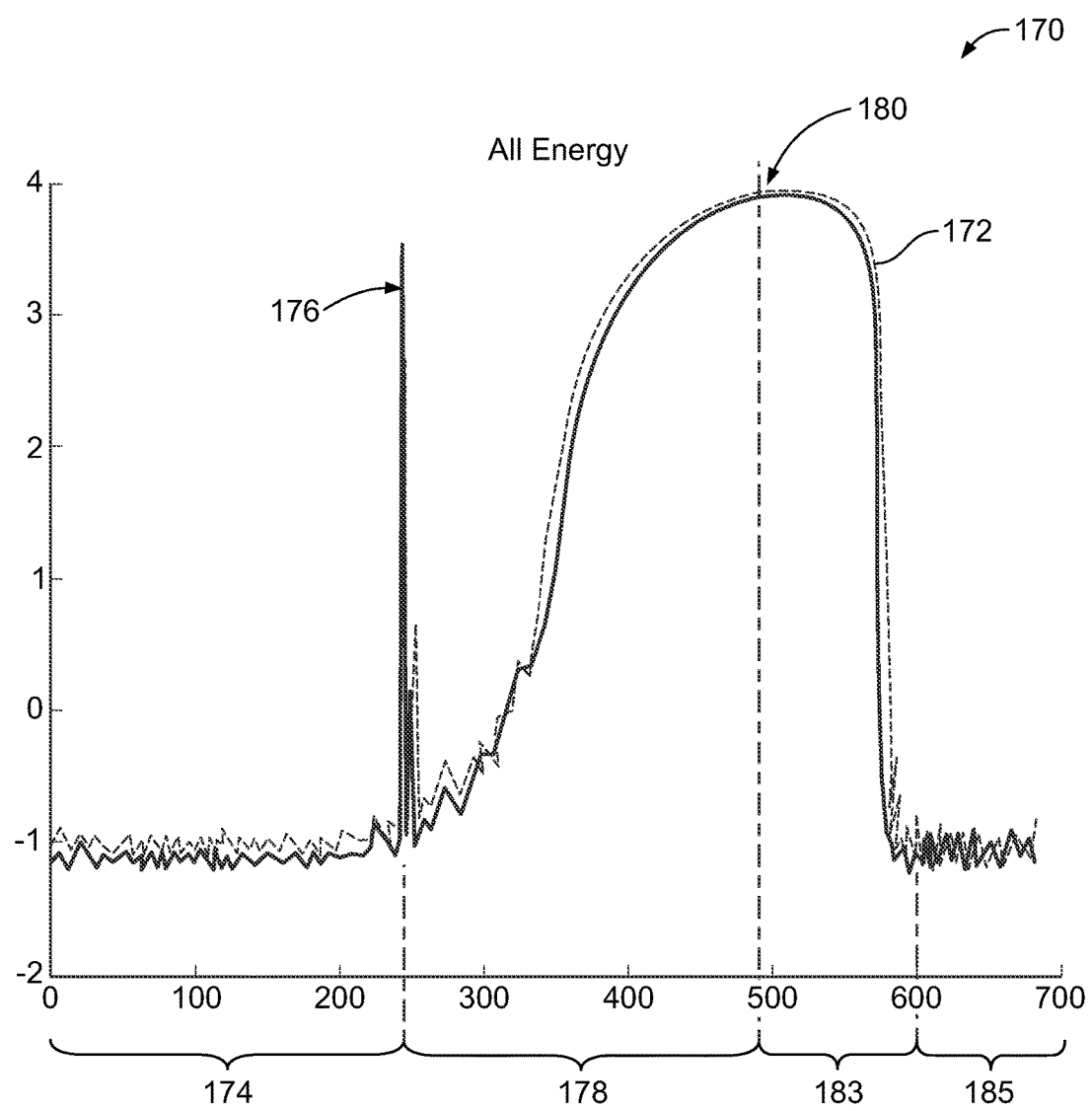
FIG. 4 is a graph of ultrasonic data taken during a crimp stroke in accordance with an embodiment.

FIG. 4 is a graph 170 of ultrasonic data taken during a crimp stroke. The graph 170 illustrates ultrasonic data from the ultrasonic transducer module 140 (shown in FIGS. 2 and 3). The data represented by the graph 170 may be used by the crimp quality module 132 (shown in FIG. 1) to determine the quality of the crimp. In the illustrated embodiment, the graph 170 shows a curve 172 representing a measure of energy associated with the ultrasonic pluses 158 (shown in FIGS. 2 and 3) plotted along the y-axis as a function of time plotted along the x-axis.

The curve 172 represents a measure of ultrasonic energy received by the ultrasonic transducer module 140 as the terminal crimping device 100 (shown in FIG. 1) moves through the various crimp phases. A region 174 represents the meeting phase whereby the ram 116 (shown in FIG. 1) moves toward the anvil 114 (shown in FIG. 1). As indicated by the region 174, the curve 172 remains substantially constant until the ram 116 (shown in FIG. 1) makes contact with the terminal 110 (shown in FIG. 1) as indicated by a peak 176. The peak 176 marks the beginning of the crimp phase indicated by a region 178. The crimp phase ends when the curve 172 reaches an approximately maximum value indicated by a peak 180. The peak 180 represents the point when the ram 116 reaches the bottom dead center. A region 183 represents the end of the retracting phase in which the ram 116 releases the terminal 110. After the ram 116 releases the terminal 110, the release phase begins, as indicated by a region 185. In the region 185, the curve 172 may have a substantial similar value as the region 174 as the ram 116 may no longer be in contact with the terminal 114.

In an embodiment, one discriminator the crimp quality module 132 may use to determine the quality of the crimp is the energy at various times when the crimp is formed. For example, the crimp quality module 132 may determine the time when the ram 116 is at the bottom dead center and use the energy value at such time. The crimp quality module 132 may determine the maximum energy value received during the crimp stroke and equate such maximum energy value with the bottom dead center. A large value of the energy may be an indication of a good crimp. More energy transmission indicates that fewer voids or other defects exist between the wire 112 (shown in FIG. 1) and the terminal 110, which reflect and/or refract the ultrasonic pulses 158 away from the ultrasonic transducer module 140. For example, the crimp quality module 132 may determine the amount of energy associated with the peak 180 representing the energy at the bottom dead center. A large energy value at the bottom dead center indicates more of the ultrasonic energy is being transmitted to and through the terminal 110 when the terminal is fully crimped.

Additionally, the crimp quality module 132 may perform coherent processing during substantially the entire crimping process of the crimp stroke from initial contact of the ram 116 with the terminal 110 until release of the ram 116 from the terminal 110. As a discriminator, the crimp quality module 132 may determine and analyze one or more frequency components of the curve 172. For example, the crimp quality module 132 may perform a Fast Fourier Transform (FFT) based on the curve 172. As another discriminator, the crimp quality module 132 may integrate, or estimate the area under the curve 172. For example, in the illustrated embodiment, the crimp quality module 132 may determine the area under the curve 172. By determining the area under the curve 172, the crimp quality module 132 can detect changes in the terminal 110 before and after the crimp is formed. As such, integration of the curve 172 allows the crimp quality module 132 to take into account changes that occur during phase transitions. Any numerical integration technique, commonly used in the art may be used to approximate the area under the curve 172 (for example, Runge-Kutta approximation, trapezoidal approximation, Simpson's approximation, and/or the like).

Optionally, the crimp quality module 132 may perform coherent processing by integrating the energy of at least a portion of the ultrasonic data associated with the crimp stroke. Integrating a portion of the curve 172 allows the crimp quality module 132 to detect defects that may not be evident in all of the crimp phases. For example, a missing strand of conductive fiber in the wire 112 may result in a reduction in the amount of energy that is transmitted through the terminal 110 during the crimping phase. This may result in the area under the curve 172 in the region 178 having a lower than expected value. In certain embodiments, the crimp quality module 132 may perform coherent processing in the area between the peak 176 and the peak 180.

The ultrasonic transducer 160 may transmit pulses over a plurality of frequency bands. The crimp quality module 132 may then filter each of the frequencies in the ultrasonic data received from the ultrasonic transducer 160 to compare features in the data to analyze the crimp quality. In other words, the crimp quality module 132 may compare the several pulses to a set of normal pulses to determine the crimp quality. The ultrasonic transducer 160 may have an operational frequency and may be configured to transmit and/or receive acoustic signals 158 in a plurality of frequency bands around the operational frequency. In an exemplary embodiment, the ultrasonic transducer 160 operates at an operational frequency of approximately 10 megahertz (MHz). For example, the ultrasonic transducer 160 may operate between 7 MHz and 13 MHz. The ultrasonic data may be filtered around the operational frequency. For example, an acquisition filter may filter the high frequencies allowing the crimp quality module 132 to analyze the lower frequencies such as between 7 MHz and 10 MHz. Alternatively, the acquisition filter may filter the low frequencies to allow the crimp quality module 132 to analyze the high frequencies such as between 10 and 13 MHz. Filtering the ultrasonic data allows certain defects that are more evident in certain frequency ranges to be exposed. For example, certain defects, such as missing strands, are more evident in low frequencies, while high frequencies makes other defects more evident. As another option, the ultrasonic transducer module 160 may transmit a plurality of pulses at predetermined frequencies, and then analyze each of the pulses individually.

Figure 5:
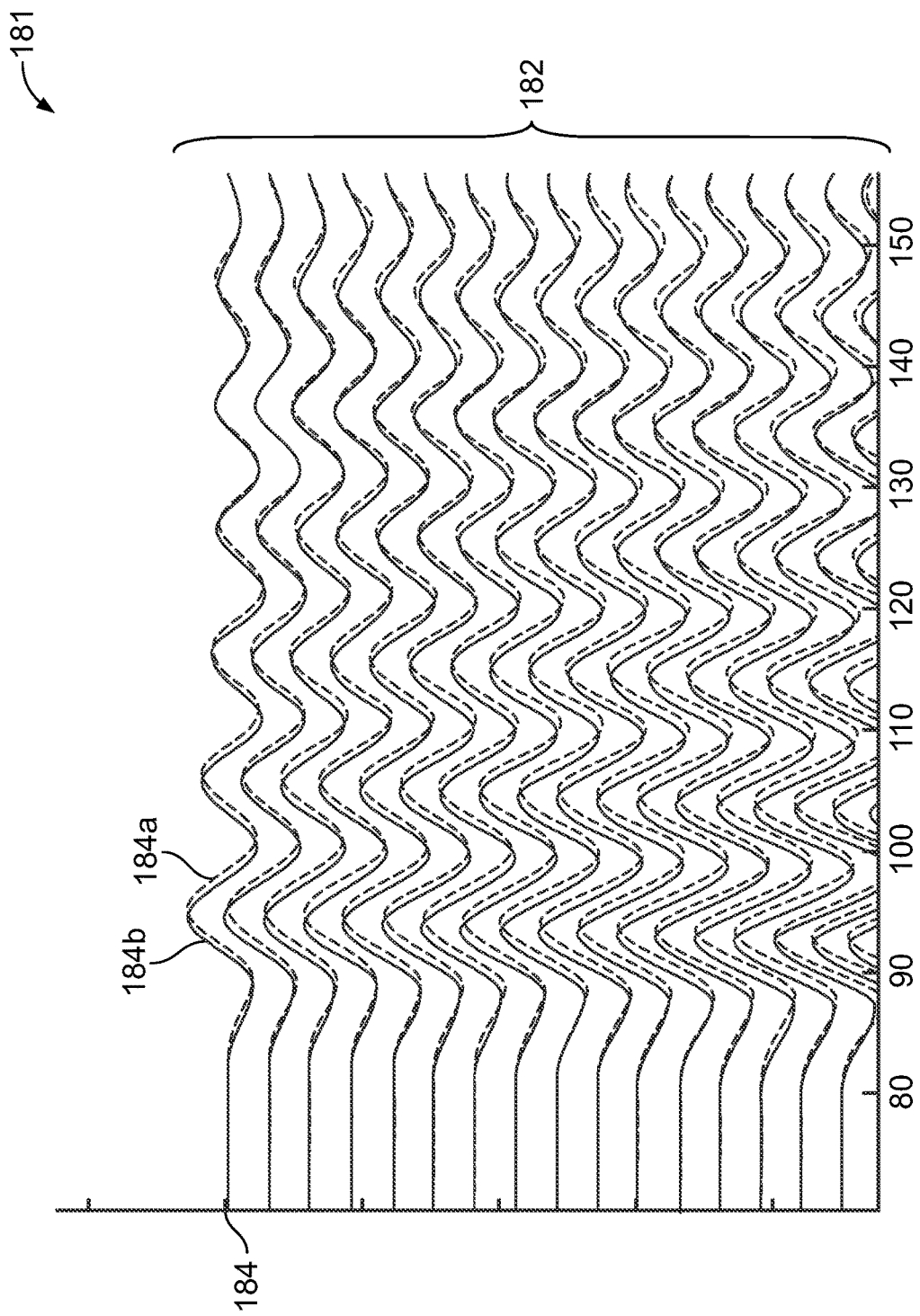
FIG. 5 is a graph showing a plurality of ultrasonic data curves showing ultrasonic data received from a plurality of pulses through a crimp stroke in accordance with an embodiment.

FIG. 5 is a graph 181 showing a plurality of ultrasonic data curves showing ultrasonic data received from a plurality of pulses through the crimp stroke. As illustrated, the graph 181 shows a set 182 of curves plotted through several crimp strokes. Each of the curves in the set 182 may be sampled at various frequencies in various frequency bands as described above. As illustrated, a first curve 184 in the set 182 includes an expected or idealistic data curve 184a representing ultrasonic data from a crimp having no faults. The actual data curve 184b represents the data received from the ultrasonic transducer 160 (shown in FIGS. 2 and 3). In the illustrated graph, the curve 184b shows data from a crimp having two missing strands. The crimp quality module 132 may use ultrasonic data from the set 182 of curves to determine the crimp quality.

The crimp quality module 132 may determine a statistical performance metric as another discriminator to determine the crimp quality. For example, statistical analysis may be used to compare the expected data curve 184a with actual data curve 184b. For example, a variance between data in the expected data curve 184a and the actual data curve 184b may be computed. The performance metric may be based on statistical analysis the plurality of ultrasonic data curves in the set 182. In an embodiment, the performance metric may be a normalized summation of the difference between the curves 184a and 184b over time and pulses. For example, Equation 1 may be used to determine the performance metric.

$$\text{Performance Metric} = \Sigma\Sigma\left(\frac{(AV - EV)^2}{Var_{EV}}\right) \quad \text{Equation 1}$$

The AV in Equation 1 may represent the ultrasonic data that comprise the actual data curve 184b, the EV may represent the ultrasonic data in the expected data curve 184a, and the $\text{Var}_{EV}$ represents the variance of the expected values. The ultrasonic data for each of the curves in the set 182 may then be summed to determine the performance metric.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

What is claimed is:

1. A terminal crimping device comprising:
   crimp tooling comprising an anvil and a ram, a crimp zone being defined between the anvil and the ram configured to receive a wire and a terminal, the crimp tooling crimping the terminal to the wire during a crimp stroke;
   an ultrasonic transducer module having at least one ultrasonic transducer held by the anvil or the ram, the ultrasonic transducer on the anvil or the ram generating a plurality of ultrasonic pulses during the crimp stroke and directing the ultrasonic pulses through the terminal, the ultrasonic transducer on the same one of the anvil or the ram receiving the ultrasonic pulses and generating ultrasonic data during the crimp stroke based on the received ultrasonic pulses; and
   a crimp quality module communicatively coupled to the ultrasonic transducer module, the crimp quality module performing coherent processing during the crimp stroke of the ultrasonic data generated during the crimp stroke to determine a crimp quality.

2. The terminal crimping device of claim 1, wherein the crimp quality module performs coherent processing during substantially an entire crimping process of the crimp stroke from initial contact of the ram with the terminal until release of the ram from the terminal.

3. The terminal crimping device of claim 1, wherein the crimp quality module performs coherent processing during a crimping process of the crimp stroke from a time period prior to bottom dead center of the crimp stroke to a time period post bottom dead center of the crimp stroke.

4. The terminal crimping device of claim 1, wherein the ultrasonic data represents an energy associated with the ultrasonic pulses.

5. The terminal crimping device of claim 4, wherein the crimp quality module performs coherent processing to determine a maximum energy received during the crimping process and determine a crimp quality based on the maximum energy.

6. The terminal crimping device of claim 4, wherein the crimp quality module performs coherent processing by integrating the energy of at least a portion of the ultrasonic data associated with the crimp stroke.

7. The terminal crimping device of claim 1, wherein the ultrasonic transducer delivers the plurality of ultrasonic pulses at a rate of at least 3 pulses during the crimping process.

8. The terminal crimping device of claim 1, wherein the crimp quality module compares several pulses to determine a performance metric, the crimp quality based on the performance metric, the performance metric including a statistical measure based on a comparison between the ultrasonic data and expected data.

9. The terminal crimping device of claim 8, wherein ultrasonic quality module performs coherent processing to determine the quality of the crimp based on at least one of an area under an energy curve, or a performance metric.

10. The terminal crimping device of claim 1, wherein the ultrasonic transducer transmits ultrasonic pulses over a plurality of frequency bands, the crimp quality module filtering the ultrasonic data in at least one of the frequency bands to determine the crimp quality.

11. The terminal crimping device of claim 1, wherein the ultrasonic transducer module includes a transmitting ultrasonic transducer and a receiving ultrasonic transducer.

12. The terminal crimping device of claim 1, wherein the at least one ultrasonic transducer is configured to operate in an echo mode, wherein the ultrasonic transducer both sends and receives the ultrasonic pulses.

13. A terminal crimping device comprising:
   crimp tooling comprising an anvil and a ram, a crimp zone being defined between the anvil and the ram configured to receive a wire and a terminal, the crimp tooling crimping the terminal to the wire during a crimp stroke; the crimp stroke having a crimping phase that begins after initial contact between the ram and the terminal to a bottom dead center of the crimp tooling, a retracting phase that begins after the bottom dead center, and a release phase that begins after the ram releases the terminal;
   an ultrasonic transducer module having at least one ultrasonic transducer held by at least one of the anvil or the ram, the ultrasonic transducer generating a plurality of ultrasonic pulses during the crimp stroke and directing the ultrasonic pulses through the terminal during the crimping phase, the ultrasonic transducer receiving the ultrasonic pulses and generating ultrasonic data during the crimp stroke based on the received ultrasonic pulses; and
   a crimp quality module communicatively coupled to the ultrasonic transducer module, the crimp quality module performing coherent processing during the crimp stroke of the ultrasonic data from the crimping phase to determine a crimp quality.

14. The terminal crimping device of claim 13, wherein the crimp quality module performs coherent processing from a time period prior to the bottom dead center at least to a time period of the bottom dead center.

15. The terminal crimping device of claim 13, wherein the crimp quality module performs coherent processing in both the crimping phase and the retracting phase.

16. The terminal crimping device of claim 13, wherein the crimp quality module performs coherent processing by integrating an energy of at least a portion of the ultrasonic data associated with the crimp stroke.

17. A terminal crimping device comprising:
crimp tooling comprising an anvil and a ram, a crimp zone being defined between the anvil and the ram configured to receive a wire and a terminal, the crimp tooling crimping the terminal to the wire during a crimp stroke;
an ultrasonic transducer module having at least one ultrasonic transducer held by at least one of the anvil or the ram, the ultrasonic transducer generating a plurality of ultrasonic pulses over a plurality of frequency bands during the crimp stroke and directing the ultrasonic pulses through the terminal, the plurality of frequency bands including a high frequency band, and a low frequency band, the ultrasonic transducer receiving the ultrasonic pulses during the crimp stroke and generating ultrasonic data based during the crimp stroke on the received ultrasonic pulses; and
a crimp quality module communicatively coupled to the ultrasonic transducer module, the crimp quality module performing coherent processing during the crimp stroke of the ultrasonic data in the frequency bands to determine a crimp quality, the crimp quality module performing filtering of the ultrasonic data in at least one of the high frequency band or the low frequency band.

18. The terminal crimping device of claim 17, wherein the crimp quality module performs coherent processing of high frequency band filtered ultrasonic data and low frequency band filtered ultrasonic data.

19. The terminal crimping device of claim 18, wherein ultrasonic quality module performs coherent processing to determine the quality of the crimp based on at least one of a maximum energy, an area under an energy curve, or a performance metric.

20. The terminal crimping device of claim 17, wherein the crimp quality module compares several pulses to determine a performance metric, the crimp quality based on the performance metric.

\* \* \* \* \*